US012690915B2

(12) United States Patent
Göttsche et al.

(10) Patent No.: US 12,690,915 B2
(45) Date of Patent: Jul. 28, 2026

(54) CATHETER

(71) Applicant: OSYPKA AG, Rheinfelden-Baden (DE)

(72) Inventors: Thorsten Göttsche, Mulhouse (FR);
Benjamin Burg, Rheinfelden (DE);
Bart Kootte, Lörrach (DE)

(73) Assignee: Osypka AG, Rheinfelden-Baden (DE)

( * ) Notice: Subject to any disclaimer, the term of this patent is extended or adjusted under 35 U.S.C. 154(b) by 938 days.

(21) Appl. No.: 17/678,146

(22) Filed: Feb. 23, 2022

(65) Prior Publication Data

US 2022/0265345 A1     Aug. 25, 2022

(30) Foreign Application Priority Data

Feb. 23, 2021     (DE) ..................... 10 2021 104 318.2

(51) Int. Cl.
*A61B 18/14*       (2006.01)
*A61B 18/00*       (2006.01)

(52) U.S. Cl.
CPC    *A61B 18/1492* (2013.01); *A61B 2018/00267* (2013.01); *A61B 2018/00577* (2013.01)

(58) Field of Classification Search
CPC ...... A61B 18/1492; A61B 2018/00267; A61B 2018/00577; A61B 2018/00839
See application file for complete search history.

(56) References Cited

U.S. PATENT DOCUMENTS

2011/0213231 A1*   9/2011   Hall ...................... A61B 5/287
                                                                600/373
2012/0209262 A1*   8/2012   Falwell ............. A61B 18/1492
                                                                606/41
2014/0236146 A1*   8/2014   McLawhorn ...... A61B 18/1492
                                                                606/41
2016/0302858 A1*   10/2016   Bencini .................. A61B 5/287

OTHER PUBLICATIONS

Bauerle, H. et al., "Pulmonary vein isolation with multipolar ablation catheters for the treatment of paroxysmal atrial fibrillation," Herzschr Elektrophys, Jun. 21, 2009, vol. 20, pp. 82-89, DOI 10.1007/s00399-009-0044-7.

* cited by examiner

*Primary Examiner* — Tigist S Demie
(74) *Attorney, Agent, or Firm* — Grogan, Tuccillo & Vanderleeden, LLP

(57)     ABSTRACT

The invention deals with improvements in the technical field of electromedical catheters. As an improvement, among other things, a catheter is proposed whose catheter arms can be clamped from an initial position into at least two different clamping positions and maintained in the clamping positions.

30 Claims, 4 Drawing Sheets

CATHETER

CROSS REFERENCE

Figure 1:
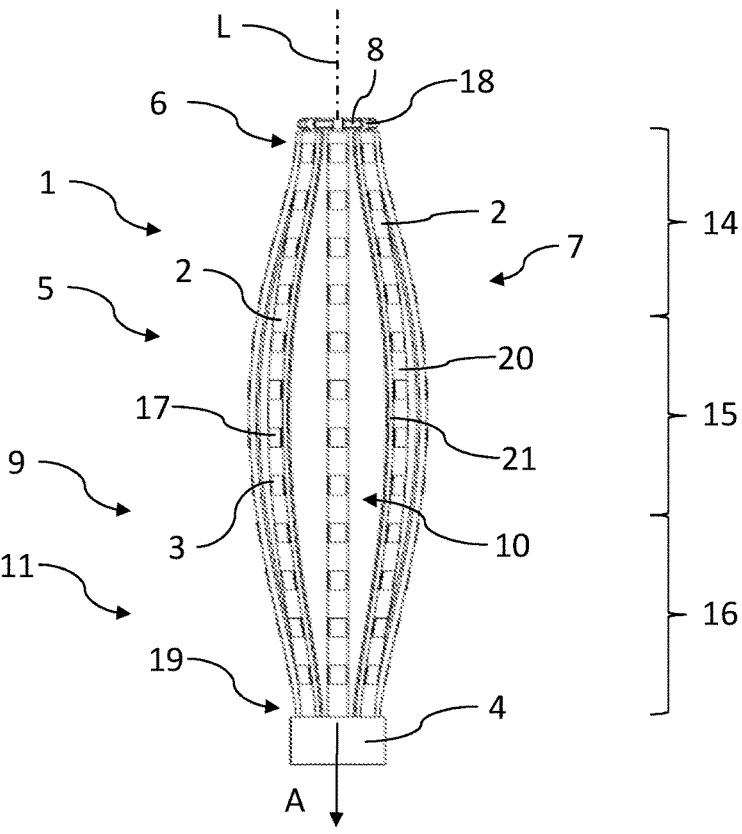

This application claims priority to German Patent Application No. 10 2021 104 318.2, filed on Feb. 23, 2021, all of which is hereby incorporated by reference in its entirety.

BACKGROUND

The invention relates to catheters with multiple catheter arms, wherein poles of electrodes are arranged on the catheter arms.

Such catheters are known from practice and are used, for example, for electromedical measurement of electrical activities in human heart tissue. In this process, catheters with their catheter arms are inserted into the heart at a target site of an electromedical measurement in order to record the electrical activities in the heart tissue. The purpose of recording electrical activity is to gain as accurate an overview as possible of electrical conduction patterns, to identify potential conduction disturbances, and ultimately to identify optimal starting points for implementing treatments to correct or mitigate conduction disturbances. In order to eliminate or limit possibly disturbed impulse conduction in the heart tissue, for example, the so-called ablation is performed, in which specific areas of tissue are destroyed.

The success of an ablation treatment also depends on the accuracy with which the conduction patterns can be detected. Accurate recording of stimulus power patterns can be complicated by the topography of the tissue being examined. Especially when strongly curved or uneven surfaces are to be examined, it is often difficult to perform a meaningful measurement, for example because a sufficient number of poles cannot be brought into contact with the target tissue. This may complicate the handling of such catheters.

It is therefore the object of the invention to provide catheters of the type mentioned above, the handling of which is simplified.

SUMMARY

To solve the object, a catheter having the features of the first independent claim directed to such a catheter is first proposed. To solve the object, it is thus proposed in particular for a catheter of the type mentioned above that it is set up to clamp the catheter arms from an initial position into at least two different clamping positions and to keep them clamped. In a first clamping position, distal ends and distal sections of the catheter arms enclose an angle of 0° to 90°, and in a second clamping position, enclose an angle of 90° to 180° with a longitudinal axis of the catheter. In the second clamping position, the distal ends and/or distal sections of the catheter arms can thus be aligned, for example, parallel to the longitudinal axis of the catheter. It is also possible for the distal ends and/or distal sections of the catheter arms to be oriented at an angle between 90° and 180° with respect to the longitudinal axis of the catheter in the second clamping position, for example at an angle of 120° or even at an angle of 178°.

Thus, the catheter arms can be clamped and kept clamped in at least two different clamping positions or configurations to perform different examinations and/or treatments. This allows for two fundamentally different basic geometric shapes of the catheter with a single catheter design. This allows an anatomy-dependent individual choice of a basic catheter shape with a specific distribution and/or arrangement of poles of the catheter in each case and thus a targeted adaptation of the catheter arms to the topography of the tissue to be examined without replacing the catheter with another catheter. This can simplify the examination and lead to more accurate examination results.

In one embodiment of the catheter, it is provided that the at least two clamping positions of the catheter arms are each at least indirectly defined by a holding position and/or a stop. The holding position and/or stop allows the person operating and guiding the catheter during treatment to receive feedback on the position of the catheter arms. In addition, the holding position and/or the stop make it possible to bring the catheter arms into the at least two different clamping positions comparatively easily and in a targeted manner.

In one embodiment of the catheter, the catheter is adapted to clamp and hold the catheter arms clamped in intermediate clamping positions even between the two different clamping positions. The previously mentioned two clamping positions of the catheter arms can be extreme positions here, beyond which the catheter is not deformed for an examination and/or treatment. Preferably, it is possible to clamp and keep the catheter arms clamped continuously in intermediate clamping positions between the two different clamping positions. In this way, the person using the catheter is offered even greater freedom of action and an even better adaptation of the catheter to the topography of the tissue to be examined is made possible.

In order to clamp the catheter arms and keep them clamped, the catheter can have a clamping device. The catheter arms may be at least indirectly interconnected at their distal ends to form a basket. For this purpose, the catheter can, for example, have a retaining plate or a retaining ring to which the catheter arms are attached by their distal end.

According to the at least two different clamping positions, the basket formed by the catheter arms can assume corresponding and different shapes in each case. Thus, the catheter may also be adapted to form its basket formed by the catheter arms in at least two different shapes.

The catheter may include a locking device for at least indirectly locking the catheter arms in the at least two different clamping positions. The locking device can be used to fix the catheter arms brought into the clamping position and keep them clamped. The locking device of the catheter can be part of the previously mentioned clamping device of the catheter.

The catheter may include a traction means, such as a traction wire and/or a traction cable. The traction means may be at least indirectly connected to the catheter arms, particularly to distal ends of the catheter arms. The traction means here can be part of the previously mentioned clamping device of the catheter. By pulling on the traction means, it is thus possible to bring the catheter arms from an unclamped initial position into one of at least two different clamping positions. If the catheter arms are connected to each other via a holder, for example the holder mentioned earlier, it may be convenient to attach the traction means to the holder.

In one embodiment of the catheter, it is provided that the traction means is disposed within a space bounded by the catheter arms. Thus, the traction device is positioned between the catheter arms, where it does not interfere with the applications and/or measurements performed with the catheter and can also be well protected from external influences.

In particular, if the catheter arms are elastic or resilient and can generate a restoring force when clamped, it is possible for the catheter arms to automatically return from their clamped positions to their initial positions. If a restoring force possibly applied by the catheter arms is not sufficient to move the catheter arms automatically from one of the at least two clamping positions back to their initial position, it is also possible to use a tension-compression means as a traction means, which can be loaded not only in tension but also in compression. In this way, the catheter arms can then be returned from one of the at least two clamping positions back to their initial position with the aid of the tension-compression means.

The catheter can have a clamping means with which the traction means can be fixed in at least two traction positions and/or in intermediate positions located between the at least two traction positions, preferably continuously. This is done with the aim of keeping the catheter arms clamped in the at least two different clamping positions and/or in intermediate clamping positions between them. The clamping means may be part of the previously mentioned clamping device and/or part of the previously mentioned locking device of the catheter.

The catheter can have at least one operating element for adjusting the catheter arms into the at least two different clamping positions. This operating element can be used to operate a clamping device, for example the one mentioned above, and/or a locking device, for example the one mentioned above. Preferably, the at least one operating element is arranged and/or formed on a proximal end and/or on a handle part of the catheter.

In a first clamping position of the at least two clamping positions, distal ends of the catheter arms may be arranged to form a distal end of the catheter. Furthermore, it is possible that in the first clamping position distal sections of the catheter arms enclose an angle between 0° and 20° with a cross-sectional plane oriented perpendicular to the longitudinal axis of the catheter. In this way, the catheter, in particular its basket formed by the catheter arms, is given a comparatively large and, above all, flat and/or level and/or largely uncurved front surface by the catheter arms held clamped in this way. This shape of the front surface may be facilitated by the catheter having no catheter elements protruding from a plane in which the front surface is formed and/or located.

Particularly preferably, the angle that the distal sections of the catheter arms enclose with the aforementioned cross-sectional plane of the catheter has a magnitude of less than 20°, for example a magnitude between 0° and 5°, particularly preferably between 0° and 2°. Ideally, the catheter arms are deformed in the first clamp position such that their distal sections are aligned at least approximately parallel or parallel to the previously mentioned cross-sectional plane of the catheter. In this way, a large front surface is created at the front side of the catheter. A comparatively high number of poles can then be available at this front surface for examination and/or treatment of the target tissue. This means that even comparatively large tissue surfaces can be examined and measured relatively quickly.

In a second clamping position of the catheter arms, distal ends and/or also distal sections of the catheter arms may be retracted between middle sections and/or proximal sections of the catheter arms. In this regard, middle sections of the catheter arms may form a distal end of the catheter, in particular a distal end of its basket comprising the catheter arms, in the second clamping position of the catheter arms. Poles arranged in the middle sections of the catheter arms thereby reach the front side of the catheter, where they are available for carrying out treatments and/or examinations. It is possible that a higher number of poles is arranged at a front side of the catheter when the catheter arms are in the first clamping position than at the front side of the catheter when the catheter arms are in the second clamping position. Of course, the exact opposite configuration is also possible, in which a smaller number of poles are then arranged on the front side of the catheter when the catheter arms are in the first clamping position than on the front side of the catheter when the catheter arms are in the second clamping position.

Outer sides of the distal sections of the catheter arms may face away from a longitudinal axis of the catheter in the initial position and/or in the first clamping position of the catheter arms. Outer sides of the distal sections of the catheter arms face the longitudinal axis of the catheter in the second clamping position.

A front surface of the catheter may be flatter and/or larger when the catheter arms are in the first clamping position than a front surface of the catheter when the catheter arms are in the second clamping position.

In order to be able to perform measurements with different resolving power with the catheter, it is possible that at least one catheter arm has at least two sections in which different pole densities can be realized and/or are realized.

In one embodiment of the catheter, it is provided that at least one catheter arm has a lower pole density in its distal section and/or in its proximal section than in its middle section. In its middle section, at least one of the catheter arms may have a higher pole density than in its distal section and/or in its proximal section. At least one catheter arm can have the same pole density in its distal section and in its proximal section.

In one embodiment of the catheter, it is provided that a higher pole density is present or formed on a front side of the catheter when the catheter arms are in the second clamping position than on the front side of the catheter when the catheter arms are in the first clamping position. If the front surface of the catheter is larger when the catheter arms are in the first clamping position, but there is less pole density at the front surface then formed at the front surface of the catheter, it is possible to measure a larger section of tissue with a slightly lower resolution. If an area of tissue of particular interest is identified during the measurement, the catheter arms can be transferred from the first clamping position to the second clamping position. It is true that the front side of the catheter may then have a smaller front surface with a possibly smaller number of poles in absolute terms. However, the poles then present there can be available in a higher pole density for a more accurate resolution measurement.

In order to be able to use the catheter not only for electromedical measurements of electrical activities in human cardiac tissue, but also for the treatment of any conduction disorders, one embodiment of the catheter provides that at least one catheter arm comprises at least one ablation pole of an ablation electrode. In this way, ablation treatments can also be performed with the catheter. Preferably, the at least one ablation pole of the ablation electrode may be located in a middle section of the catheter arm. As previously mentioned, when the catheter arms are in the second clamping position, the middle sections of the catheter arms can form a distal end of the catheter. In particular, if the middle sections also have a higher pole density, it becomes possible, after a comparatively rough examination of the target tissue with the catheter arms held clamped in the first clamping position, to first perform a finer examination of the target tissue with the increased pole density at the front side of the catheter with the catheter arms in the second clamping position. Once an area of tissue requiring treatment has been identified, the at least one ablation pole, which is preferably also disposed in the middle section of at least one catheter arm, can be brought into contact with the area of tissue and ablation treatment of the area of tissue can be performed. Such a configuration of the catheter may promote efficient identification and treatment of conduction disorders.

To solve the task, in one embodiment of the catheter, it is provided that at least one catheter arm has at least one joint. The at least one joint can have a degree of freedom of one and/or be designed as a swivel joint.

As previously discussed, the catheter arms of such catheters can often be clamped from an initial position that may favor their application to the target tissue. In the process, the catheter arms can be subjected to comparatively high alternating loads, which in the worst case can cause the catheter arms to break. In order to reduce the stresses on the catheter arms, it is proposed according to the invention that at least one catheter arm of the catheter has at least one joint. Preferably, several catheter arms or even all catheter arms of the catheter have at least one joint.

In one embodiment of the catheter, it is provided that at least one catheter arm includes a joint disposed between a distal end and a proximal end of the catheter arm. This can reduce stress in the middle section of a catheter arm.

Particularly in connection with the previously described catheter, which is the subject of the independent claim, it is advantageous if at least one catheter arm has a joint at its distal end. The catheter arm may be at least indirectly connected to at least one other catheter arm via the joint. In this way, the mobility of the catheter arms can be favored and the catheter arms can be protected from overloading.

Preferably, several catheter arms or all catheter arms are also provided with joints at their distal ends, via which they are at least indirectly connected to at least one other catheter arm. In one embodiment of the catheter, it is provided that the catheter arms are each connected via a joint to a holder, for example to the previously mentioned holder, which is formed, for example, as a retaining plate and/or retaining ring.

In one embodiment of the catheter, it is provided that at least one catheter arm has a joint at its proximal end, via which it is at least indirectly connected to at least one other catheter arm. It is also possible that several catheter arms or all catheter arms have joints at their proximal ends, via which they are at least indirectly connected to at least one other catheter arm. The joints help bring the catheter arms into different positions under as little stress as possible, thereby forming baskets of catheter arms that have different geometries.

If at least one catheter arm of the catheter has a joint at its distal end and one at its proximal end, this aids the formation of a spherical basket of catheter arms. It is particularly easy to form a spherical basket if several or all of the catheter arms have a joint at their distal ends and a joint at their proximal ends.

The at least one joint of the catheter arm may be a film hinge, for example. The joint, which is designed as a film hinge, can have a material weakening running along its pivot axis. It is possible that the at least one joint is at least partially made of plastic and/or metal.

In any of the previously described embodiments of catheters, it may be provided that at least one catheter arm is formed at least in part from a flexible circuit board material. Leads of the electrodes as well as the poles can be or are comparatively easily applied to the flexible printed circuit board material of the at least one catheter arm.

At least one catheter arm may have a preferably metallic support layer on which, for example, at least one pole and/or, for example, the previously mentioned flexible printed circuit board material of the catheter arm may be applied. The support layer can give the catheter arm its required stability and also a certain resilience. For example, a strip of material, preferably a strip of sheet metal, can serve as the support layer. Printed circuit board foil can be used as the printed circuit board material.

The at least one joint can have a pivot range of up to 180°. This may facilitate movement of the distal ends and/or sections of the catheter arms to the angular positions of 0° to 90° in the first clamping position and 90° to 180° in the second clamping position relative to the longitudinal axis of the catheter, as previously described in detail.

The invention will now be described in more detail with reference to an exemplary embodiment, but is not limited to this exemplary embodiment. Further embodiments result from combining the features of individual or several claims of protection with each other and/or with individual or several features of the exemplary embodiment.

DRAWINGS

Figure 2:
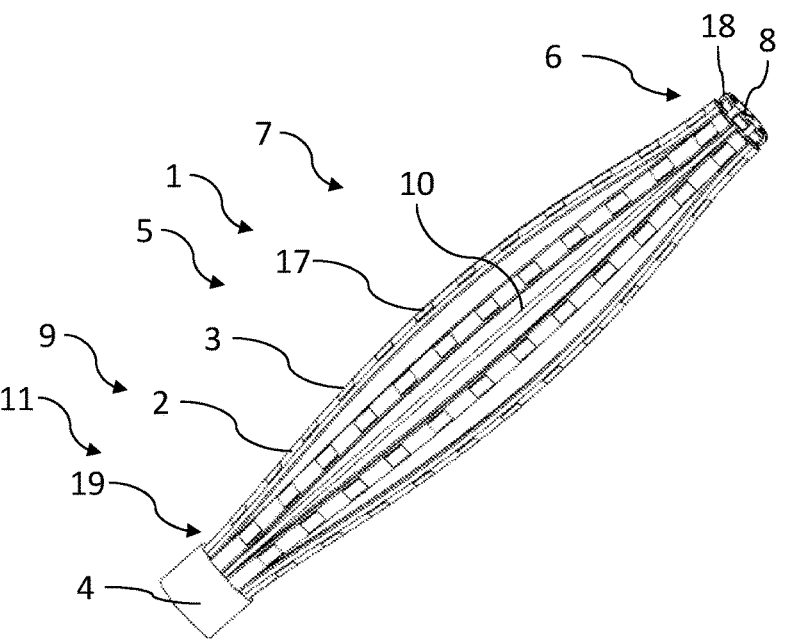
Figure 3:
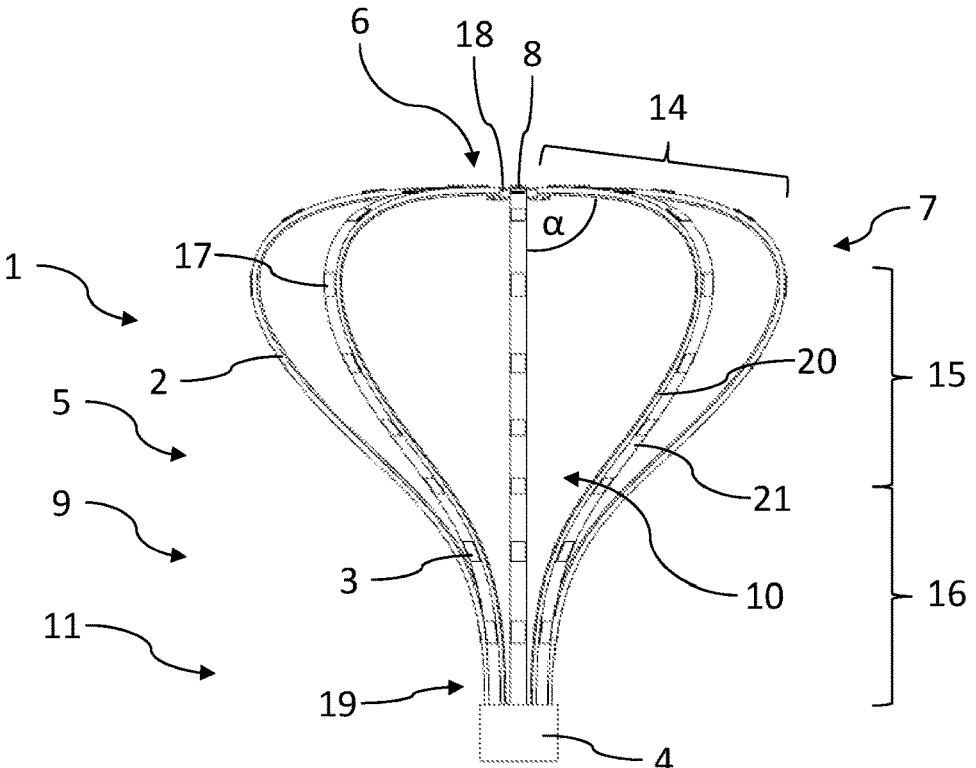
Figure 4:
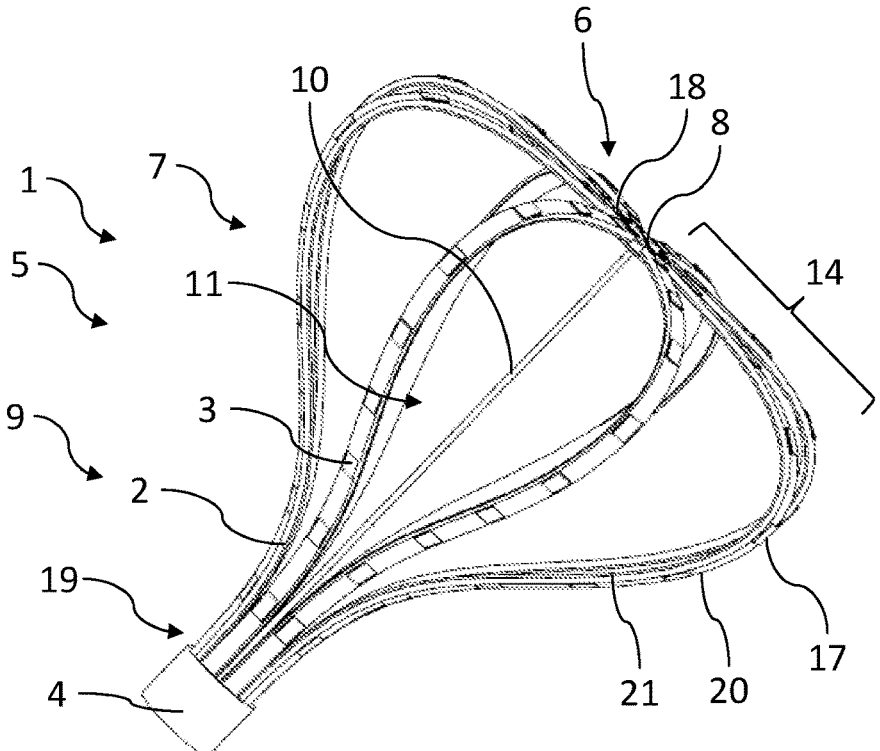
Figure 5:
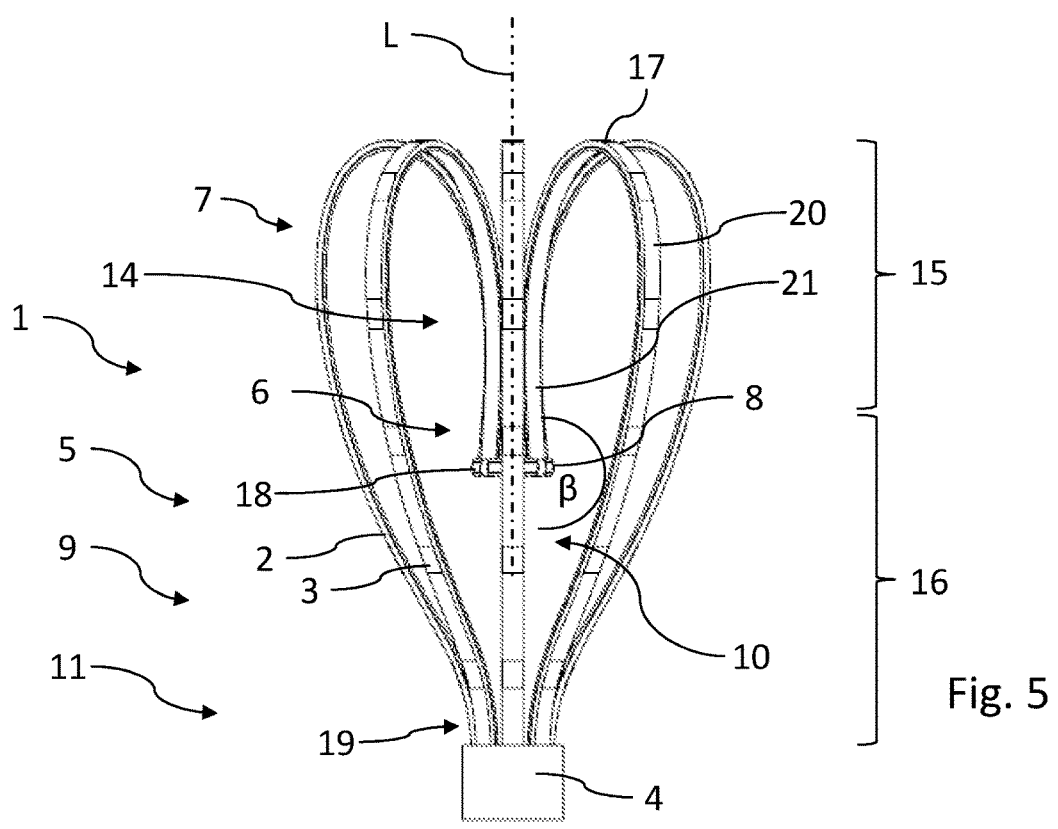
Figure 6:
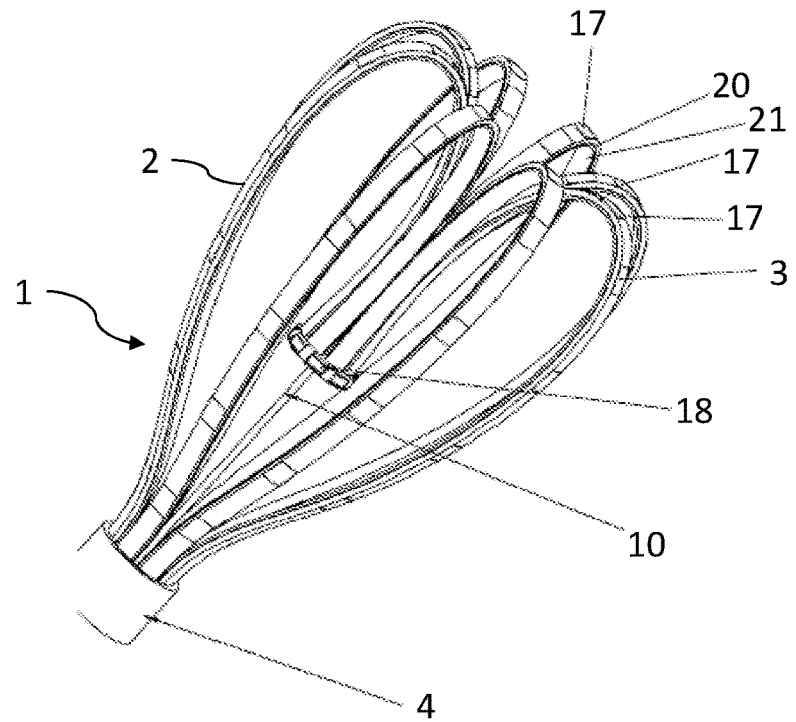
Figure 7:
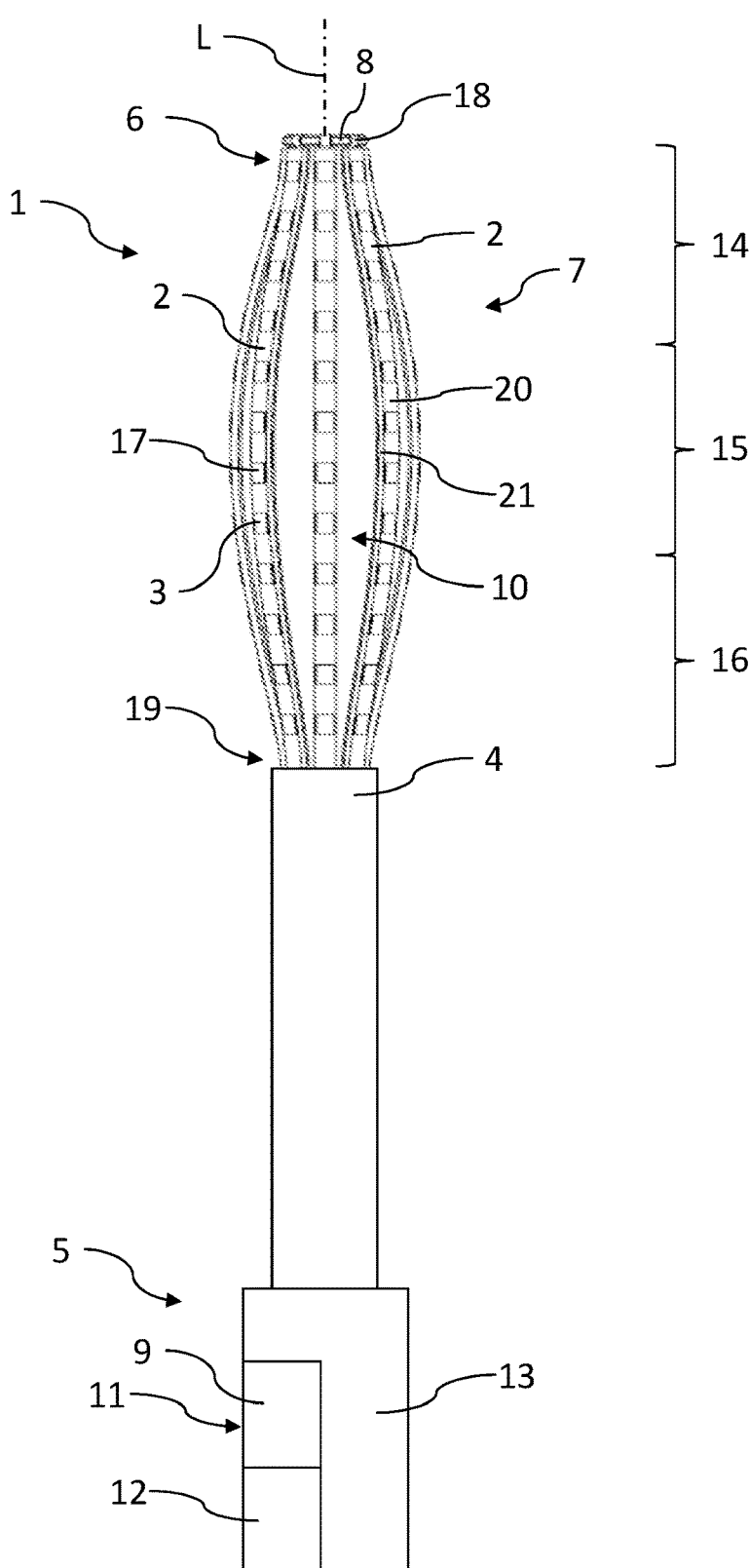

The present invention will be better understood from reading the following description of non-limiting embodiments, with reference to the attached drawings, wherein below:

FIG. 1: a side view of an end section of a catheter with catheter arms in the unclamped initial position, FIG. 2: a perspective view of the end section shown in FIG. 1, FIG. 3 a side view of the end section shown in the previous figures with catheter arms in a first clamping position, FIG. 4: a perspective view of the end section shown in FIG. 3, FIG. 5 a side view of the end section shown in the previous figures with catheter arms in a first clamping position, FIG. 6 a perspective view of the end section shown in FIG. 5, and FIG. 7 a side view, highly simplified in parts, of a catheter equipped with the end section shown in the previous figures.

DETAILED DESCRIPTION

All figures show at least parts of a catheter, indicated in its entirety by 1. The catheter 1 is adapted to perform electromedical measurements in the human heart to monitor electrical activity in cardiac tissue and identify conduction disturbances, if any.

The catheter 1 has a plurality of catheter arms 2 on which poles 3 of electrodes are arranged. With the aid of the poles 3, the electrical activities in the human heart tissue can be recorded and transmitted to an evaluation unit.

The catheter 1 is adapted to clamp and hold the catheter arms 2 clamped from an initial position shown in FIGS. 1 and 2 in at least two different clamping positions.

FIGS. 1 and 2 show an embodiment of the catheter 1 with its catheter arms 2 in an initial position in which the catheter arms 2 are unclamped, or at least almost unclamped. In this position, the catheter arms 2 can be guided through a shaft 4 of the catheter 1 to a target location, such as a human heart. The initial position assumed by the catheter arms 2 according to FIG. 1 is not a clamping position in the sense of the invention. The at least two different clamping positions may also be referred to as two different use positions of the catheter arms 2.

In the first clamping position according to FIG. 3, the distal ends 6 and the distal sections 14 enclose an angle α of 0° to 90°, in this case an angle α of 90° with a longitudinal axis L of the catheter 1. In the second clamping position according to FIG. 5, the distal ends 6 and the distal sections 14 enclose an angle of 90° to 180°, here an angle β of 180°, with the longitudinal axis L of the catheter 1. Thus, in the first clamping position, the distal ends 6 and the distal sections 14 of the catheter arms 2 are aligned at a right angle, and in the second clamping position, they are aligned parallel to the longitudinal axis L.

The at least two clamping positions of the catheter arms 2 are each at least indirectly defined by a holding position and/or a stop.

The catheter 1 is adapted to clamp the catheter arms 2 continuously in intermediate clamping positions between the two different clamping positions and to keep them clamped in these intermediate clamping positions.

Depending on which intermediate clamping position or clamping position the catheter arms 2 assume, the end section of the catheter 1, which may also be referred to as the catheter tip, takes on different shapes.

In order to clamp the catheter arms 2 and keep them clamped in the different positions, the catheter 1 is equipped with a clamping device 5.

The catheter arms 2 are indirectly interconnected at their distal ends 6 to form a basket 7 via a holder 8. The basket 7 is shown in a first form in FIGS. 3 and 4, and in a second form in FIGS. 5 and 6. The holder 8 of the catheter 1 shown in the figures is a retaining ring. In an embodiment of the catheter 1 not shown in the figures, the holder 8 is a retaining plate.

FIGS. 3 and 4 show the catheter 1 with its catheter arms 2 in the first clamping position. As a result, the basket 7 formed by the catheter arms 2 has a corresponding first shape.

In FIGS. 5 and 6, the catheter arms 2 are shown in their second clamping position, in which the basket 7 of the catheter 1 has assumed a corresponding second shape or form.

The catheter 1 further comprises a locking device 9, which is part of the clamping device 5. The locking device 9 serves to at least indirectly lock the catheter arms 2 in the at least two different clamping positions. By means of a traction means 10, which can be designed as a traction wire and/or also as a traction cable, the catheter arms 2 can be moved from their initial position shown in FIGS. 1, 2 and 7 into the clamping positions shown in FIGS. 3 to 6.

The traction means 10 is attached to the holder 8 and thereby connected at least indirectly to the distal ends 6 of the catheter arms. The traction means 10 extends through a space bounded by the catheter arms 2 and is thus disposed between the catheter arms 2. By pulling on the traction means 10 in the direction of the arrow A, the catheter arms 2 can be moved from the initial position to the clamping positions. The resetting of the catheter arms 2 takes place opposite the direction of arrow A.

The locking device 9 of the catheter 1 comprises a clamping means 11, with which the traction means 10 can be continuously fixed in different traction positions. In this way, the catheter arms 2 can be kept clamped in their various clamping positions and also in the intermediate clamping positions between them.

For the operation of its clamping device 5 and also its locking device 9, the catheter 1 has at least one corresponding operating element 12, which is arranged or formed in or on a handle part 13 of the catheter 1 and is shown in highly schematized form in FIG. 7.

FIGS. 3 and 4 illustrate that the distal ends 6 of the catheter arms 2 form a distal end of the catheter 1 in the first clamping position. In the first clamping position, distal sections 14 of the catheter arms 2 are clamped parallel or nearly parallel to a cross-sectional plane oriented at right angles to the longitudinal axis L of the catheter 1, and in the embodiment described herein, this is such that no design and/or construction elements of the catheter 1 protrude from this cross-sectional plane in the direction of the longitudinal axis L of the catheter 1. In the first clamping position, the distal sections 14 of the catheter arms 2 can enclose an angle between 0° and 20° with the previously mentioned cross-sectional plane. Preferably, however, in the first clamping position they enclose an angle with the cross-sectional plane that is less than 20°, for example between 0° and 5°, preferably between 0° and 2°.

FIGS. 5 and 6 illustrate that the distal ends 6 and also the distal sections 14 of the catheter arms 2 are arranged retracted between middle sections 15 and/or also proximal sections 16 of the catheter arms 2 in the second clamping position. While the outer sides of the distal sections 14 of the catheter arms 2 face away from the longitudinal axis L of the catheter 1 in the initial position and also in the first clamping position of the catheter arms 2, they are inverted and face the longitudinal axis L of the catheter 1 in the second clamping position.

In the second clamping position, at least parts of the middle sections 15 of the catheter arms 2 form the distal end of the catheter 1. In absolute terms, a larger number of poles 3 are arranged on one front side of the catheter 1 when the catheter arms 2 are in the first clamping position than on the front side of the catheter 1 when the catheter arms 2 are in the second clamping position.

A front surface of the catheter 1 formed by the distal sections 14 when the catheter arms 2 are in the first clamping position, as shown in FIGS. 3 and 4, is flatter and also larger than a front surface of the catheter 1 formed by parts of the middle sections 15 of the catheter arms 2, as shown in FIGS. 5 and 6, when the catheter arms 2 are in the second clamping position.

Each of the catheter arms 2 may, in one embodiment of the catheter 1, have at least two sections in which different pole densities are realized. In the distal sections 14 and in the proximal sections 16 of the catheter arms 2, the same pole density is then realized in each case, but a lower pole density than in the middle sections 15 of the catheter arms 2. Thus, higher pole densities are available in the middle sections 15 than in the other sections 14 and 16 of the catheter arms 2.

As a result, a higher pole density is formed on one front side of the catheter 1 when the catheter arms 2 are in the second clamping position than on the front side of the catheter 1 when the catheter arms 2 are in the first clamping position.

The catheter arms 2 each have at least one ablation pole 17 of an ablation electrode in their middle sections 15. Via the ablation pole 17, it is possible to deliver electrical pulses for ablation of an area of tissue. In the second clamping position of the catheter arms 2, the ablation poles 17 reach the distal end of the catheter 1, where they are ready for ablation of an area of tissue requiring treatment.

To aid in the mobility of the catheter arms 2 and to protect the catheter arms 2 from damage as they are moved back and forth between the different clamping positions, each of the catheter arms 2 has a joint 18 at its distal end 6.

Via their joints 18, the catheter arms 2 are connected at least indirectly, namely here via the holder 8, to the other catheter arms 2. Each of the catheter arms 2 is connected to the holder 8 via its joint 18 located at its distal end 6.

In an embodiment of the catheter 1 not shown in the figures, it is provided that at least one of the catheter arms 2 has at least one joint 18 arranged between the distal end 6 and a proximal end 19 of the catheter arm 2. The joints 18 can be designed as film hinges and/or be at least partially made of plastic and/or metal. The joints 18 each have a pivot range of up to 180°, which facilitates adjustment of the catheter arms 2 into and between clamping positions.

In one embodiment of the catheter 1, it is provided that at least one further joint is also attached to the proximal end 19 of the catheter arms 2. Thus, at least one of the catheter arms 2 may be supported by two joints 18, for example in the form of integral hinges. This allows the catheter arms 2 to be oriented at the proximal end 19 as they are at the distal end 6—for example, in a cross-sectional plane oriented perpendicular to the longitudinal axis L of the catheter 1. Joints 18 at the proximal ends 19 of the catheter arms 2 favor arranging the catheter arms 2 in such a way that their proximal ends 19 and the proximal sections adjacent thereto can enclose an angle of 0° to 90° with the longitudinal axis L of the catheter 1 in a first clamping position and an angle of 90° to 180° in a second clamping position.

The catheter arms 2 of the catheter 1 shown in the figures are made at least in part of a flexible printed circuit board material. The flexible conductor material forms an outer support layer 20 of the catheter arms 2 facing away from the longitudinal axis L of the catheter 1 in the initial position of the catheter arms 2.

The outer support layer 20 made of printed circuit board material is reinforced on the inside by an inner support layer 21, which in the shown exemplary embodiment of the catheter 2 is made of metal. Due to the metallic and internal support layer 21, the catheter arms 2 become resilient, so that they move automatically from their clamping positions shown in FIGS. 3 to 6 back to their initial position shown in FIGS. 1, 2 and 7 as soon as they are no longer being pulled and/or held by the traction means 10.

The invention deals with improvements in the technical field of electromedical catheters. As an improvement, among other things, a catheter 1 is proposed whose catheter arms 2 can be clamped from an initial position into at least two different clamping positions and kept clamped there.

What is claimed is:

1. A catheter (1) for electromedical measurement of electrical activities in human heart tissue, the catheter comprising:
   a plurality of catheter arms (2), the catheter arms (2) have poles (3) of electrodes arranged thereon; and
   wherein the catheter (1) is configured to clamp the catheter arms (2) from an initial position into at least two different clamping positions and to keep them clamped; and
   wherein distal ends (6) and/or distal sections (14) of the catheter arms (2) form an angle (a) of 0 to 90 with a longitudinal axis (L) of the catheter (1) in a first clamping position, and an angle (3) of 90 to 180 in a second clamping position;
   wherein the catheter arms (2) are made at least in part of a flexible printed circuit board material forming an outer support layer; and wherein, in the first clamping position, outer sides of the distal sections (14) of the catheter arms (2) face away from the longitudinal axis (L) of the catheter (1); and
   wherein, in the second clamping position, the distal ends (6) and/or distal sections (14) of the catheter arms are arranged retracted substantially between middle sections (15) and proximal sections (16) of the catheter arms, and the outer sides of the distal sections (14) of the catheter arms (2) face the longitudinal axis (L) of the catheter (1).

2. The catheter (1) of claim 1, wherein the at least two clamping positions of the catheter arms (2) are each at least indirectly defined by a holding position and/or a stop.

3. The catheter (1) of claim 1, wherein the catheter (1) is configured to clamp and keep clamped the catheter arms (2) between the two different clamping positions in intermediate clamping positions.

4. The catheter (1) of claim 1, wherein the catheter (1) further comprises a clamping device (5) for clamping and keeping the catheter arms (2) clamped.

5. The catheter (1) of claim 1, wherein the catheter arms (2) are at least indirectly interconnected at their distal ends (6) to form a basket (7) via a holder (8).

6. The catheter (1) of claim 5, wherein the holder (8) is a retaining plate or a retaining ring.

7. The catheter (1) of claim 1, wherein the catheter (1) includes a locking device (9) for locking the catheter arms (2) in the at least two different clamping positions.

8. The catheter (1) of claim 1 wherein the clamping device (5) of the catheter (1) comprises:
   a traction means (10) operatively to distal ends (6) of the catheter arms (2) and is arranged within a space delimited by the catheter arms (2).

9. The catheter (1) of claim 8 wherein the traction means (10) is a traction wire or a traction cable.

10. The catheter (1) of claim 1, wherein the catheter (1), in particular its locking device (9), has a clamping means (11) with which the traction means (10) can be fixed in at least two traction positions and/or in intermediate positions located between the at least two traction positions in order to keep the catheter arms (2) clamped in the at least two different clamping positions and/or in intermediate clamping positions located between the two clamping positions.

11. The catheter (1) of claim 1, wherein the catheter (1) has at least one operating element (12) with which one of the clamping device (5) and/or one or the locking device (9) can be operated; and
   wherein the operating element (12) is located at a proximal end and/or in or on a handle part (13) of the catheter (1).

12. The catheter (1) of claim 1 wherein distal ends (6) of the catheter arms (2) form a distal end of the catheter (1) in a first clamping position and/or wherein distal sections (14) of the catheter arms (2) form an angle between 0° and 20° with a cross-sectional plane oriented at right angles to the longitudinal axis (L) of the catheter (1) in the first clamping position.

13. The catheter (1) of claim 12 wherein the angle is between 0° and 5°.

14. The catheter (1) of claim 12 wherein the angle is between 0° and 2°.

15. The catheter (1) of claim 1, wherein a higher number of poles (3) is arranged on a front side of the catheter (1) when the catheter arms (2) are in the first clamping position than on the front side of the catheter (1) when the catheter arms (2) are in the second clamping position.

16. The catheter (1) of claim 1 wherein when the catheter arms (2) are in the first clamping position a front surface of the catheter (1) is flatter and/or larger than a front surface of the catheter (1) when the catheter arms (2) are in the second clamping position.

17. The catheter (1) of claim 1, wherein at least one catheter arm (2) has at least two sections in which different pole densities are realizable.

18. The catheter (1) of claim 1, wherein at least one catheter arm (2) has a higher pole density in its middle section (15) than in its distal section (14) and/or in its proximal section (16).

19. The catheter (1) of claim 18, wherein at least one catheter arm (2) has the same pole density in its distal section (14) and in its proximal section (15).

20. The catheter (1) of claim 1, wherein a higher pole density is formed on the front side of the catheter (1) when the catheter arms (2) are in the second clamping position than on a front side of the catheter (1) when the catheter arms (2) are in the first clamping position.

21. The catheter (1) of claim 1, wherein at least one catheter arm (2) has, in its middle section (15), at least one ablation pole (17) of an ablation electrode.

22. The catheter (1) of claim 1, wherein at least one catheter arm (2) comprises at least one joint (18).

23. The catheter (1) of claim 22, wherein the at least one joint (18) is an integral hinge and/or consists at least partially of plastic and/or of metal.

24. The catheter (1) of claim 22, wherein the at least one joint (18) of the catheter (1) has a pivot range of up to 180°.

25. The catheter (1) of claim 1, wherein several catheter arms (2) or all catheter arms (2) comprise at least one joint (18).

26. The catheter (1) of claim 1, wherein at least one catheter arm (2) has a joint (18) at its distal end (6), via which it is at least indirectly connected to at least one other catheter arm (2), or wherein several catheter arms (2) or all catheter arms (2) have joints (18) at their distal ends (6), via which they are at least indirectly connected to at least one other catheter arm (2).

27. The catheter (1) of claim 1, wherein at least one catheter arm (2) has a joint (18) at its proximal end (19), via which it is at least indirectly connected to at least one other catheter arm (2), or wherein several catheter arms (2) or all catheter arms (2) have joints (18) at their proximal ends (6), via which they are at least indirectly connected to at least one other catheter arm (2).

28. The catheter (1) of claim 1, wherein at least one catheter arm (2) has a joint (18) at its distal end (6) and at its proximal end (19), respectively, or wherein several or all catheter arms (2) have a joint (18) at their distal ends (6) and at their proximal ends (19), respectively.

29. The catheter (1) of claim 1, wherein at least one catheter arm (2) comprises a joint (18) arranged between a proximal end (6) and a distal end (19) of the catheter arm (2).

30. The catheter (1) of claim 1, wherein at least one catheter arm (2) is formed at least in part from a flexible printed circuit board material and/or wherein at least one catheter arm (2) comprises a metallic support layer (21).

* * * * *